United States Patent
Candelore

(10) Patent No.: US 7,117,534 B2
(45) Date of Patent: Oct. 3, 2006

(54) INTERFACING A CONDITIONAL ACCESS CIRCUIT TO A DIGITAL DEVICE USING INPUT AND OUTPUT STREAM SWITCHING

(75) Inventor: Brant L. Candelore, Escondido, CA (US)

(73) Assignees: Sony Corporation, Tokyo (JP); Sony Electronics Inc., Park Ridge, NJ (US)

( * ) Notice: Subject to any disclaimer, the term of this patent is extended or adjusted under 35 U.S.C. 154(b) by 580 days.

(21) Appl. No.: 10/909,887

(22) Filed: Apr. 8, 2003

(65) Prior Publication Data

US 2005/0002385 A1 Jan. 6, 2005

Related U.S. Application Data

(63) Continuation of application No. 09/416,920, filed on Oct. 13, 1999.

(60) Provisional application No. 60/126,865, filed on Mar. 30, 1999.

(51) Int. Cl.
*H04L 9/00* (2006.01)

(52) U.S. Cl. ............................ 726/26; 726/27; 726/30; 726/32

(58) Field of Classification Search ........ 380/200–201, 380/203–204, 241; 713/174, 193, 189; 705/57; 726/26–27, 32, 30; 710/200; 370/537
See application file for complete search history.

(56) References Cited

U.S. PATENT DOCUMENTS 5,282,249 A * 1/1994 Cohen et al. ................ 380/229

FOREIGN PATENT DOCUMENTS

EP 0858184 A2 * 12/1998
EP 0893765 A1 * 1/1999

* cited by examiner

*Primary Examiner*—Hosuk Song
(74) *Attorney, Agent, or Firm*—Blakely, Sokoloff, Taylor & Zafman LLP

(57) ABSTRACT

The present invention is a method and apparatus for interfacing a host and a conditional access circuit to a digital device. A switching circuit is coupled to the host and the conditional access circuit to switch input streams into output streams. The input streams include a host stream from the host and the output streams include an interface output stream. An interface circuit is coupled to the steering circuit and the digital device to transfer the interface output stream to the digital device.

30 Claims, 6 Drawing Sheets

INTERFACING A CONDITIONAL ACCESS CIRCUIT TO A DIGITAL DEVICE USING INPUT AND OUTPUT STREAM SWITCHING

RELATED APPLICATIONS

This application is a continuation of application Ser. No. 09/416,920 filed Oct. 13, 1999, which is a utility of provisional patent application No. 60/126,865 filed Mar. 30, 1999.

BACKGROUND

1. Field of the Invention

The present invention is related to conditional access devices. In particular, the present invention is related to interfacing a conditional access device to a digital device.

2. Description of Related Art

Modern set-top boxes generally have a receiver to receive program data, or content, from a service provider and generate multiple transport streams. The content is normally scrambled before being transmitted to the receiver. The scrambled content is then de-scrambled by a conditional access (CA) device. Currently, entitlement management messages (EMM) typically use unique keys or signatures to deliver a group key or access parameters to CA devices. An EMM is a message used to deliver privileges (e.g., rights, keys) to a CA device. Typically the group are users or customers who share a particular set of entitlements. The National Renewable Security System (NRSS) defines two types of CA devices or modules: an NRSS part A module supporting a smart card form factor, and an NRSS part B module supporting a PCMCIA form factor.

The unscrambled content is then transferred or downloaded to a digital device such as a display device (e.g., digital television) for program viewing or a recording device (e.g., digital video cassette recorder) for program recording. In many scenarios, multiple digital devices are connected to the conditional access device for simultaneous activities such as viewing while recording or viewing at different display locations.

A standardized interface between the conditional access device and the digital device is desirable. However, it is important to safeguard the content or transport streams from unauthorized copying by the digital device. In addition, the interface should be flexible enough to accommodate several usage options such as store and playback.

Therefore, there is a need to have an efficient and flexible technique to interface a conditional access device to a digital device.

SUMMARY

The present invention is a method and apparatus for interfacing a host and a conditional access circuit to a digital device, A switching circuit is coupled to the host and the conditional access circuit to switch input streams into output streams. The input streams include a host stream from the host and the output streams include an interface output stream. An interface circuit is coupled to the steering circuit and the digital device to transfer the interface output stream to the digital device.

BRIEF DESCRIPTION OF THE DRAWINGS

The features and advantages of the present invention will become apparent from the following detailed description of the present invention in which.

DESCRIPTION

The present invention is a method and apparatus to interface a host and a conditional access circuit to a digital device. A switching circuit is coupled to the host and the conditional access circuit to switch input streams into output streams. The input streams include a host stream from the host. The output streams include an interface output stream. An interface circuit is coupled to the switching circuit and the digital device to transfer the interface output stream to the digital device. The conditional access circuit includes a de-scrambler and a copy protection circuit. The de-scrambler receives a de-scrambler input stream and generates a de-scrambled stream. The output streams further include a copy stream to the copy protection circuit and the de-scrambler input stream to the de-scrambler. The input streams further include the de-scrambled stream from the de-scrambler and an interface input stream from the interface circuit.

In one embodiment, the switching circuit comprises a first switching element coupled to the host and the de-scrambler to provide the interface output stream from an internal stream and the de-scrambled stream; and a second switching element coupled to the digital device, the copy protection circuit and the de-scrambler to provide the copy stream from the de-scrambled stream and the interface input stream.

The switching and interface circuit provides flexibility in data routing for input and output streams to support a variety of platforms, configurations, or environments.

In the following description, numerous specific details are set forth in order to provide a thorough understanding of the present invention. It will be apparent, however, to one of ordinary skill in the art that the present invention may be practiced without these specific details. In other instances, well-known architectures, steps, and techniques have not been shown where unnecessary for an understanding of the present invention. For example, specific details are not provided as to whether the method is implemented in a station as a software routine, hardware circuit, firmware, or a combination thereof. The term "stream" refers to a transport stream which is typically in a digital form.

Figure 1:
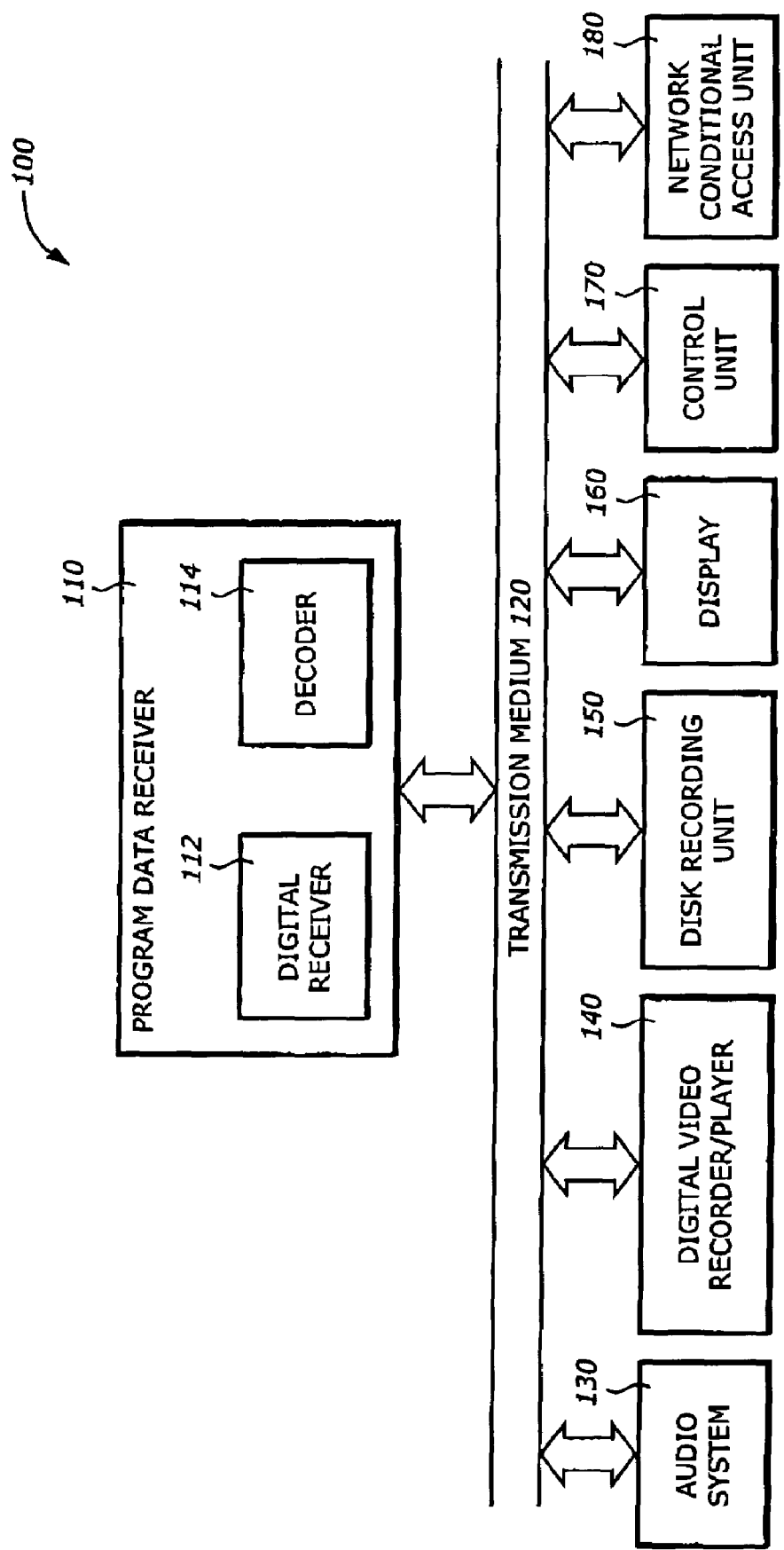
FIG. 1 is a diagram illustrating a system in which one embodiment of the invention can be practiced.

FIG. 1 is a diagram illustrating a system 100 in which one embodiment of the invention can be practiced. The system 100 includes a program data receiver 110, a transmission medium 120, an audio system 130, a digital video recorder or player 140, a disk recording unit 150, a display 160, a control unit 170, and a network CA unit 180. Any of the audio system 130, the digital video recorder or player 140, the disk recording unit 150, the display 160 and the control unit 170, or any combination thereof may be referred to as a digital device.

The program data receiver 110 includes a digital receiver 112 and a decoder 114. The digital receiver 112 receives digital bitstream or data including program data from one or more service providers. Such service or content providers may include terrestrial broadcasters, cable operators, direct broadcast satellite (DBS) companies, companies providing content for download via the Internet, book publisher, software companies distributing software products, or any similar content and/or service provider. The program data may include system information, entitlement control messages, entitlement management messages, content, and other data. System information may include information on program names, time of broadcast, source, method of retrieving and decoding, copy management commands that provide digital receivers and other devices that control how, when, and what program data may be replayed, retransmitted, copied, and/or recorded. These copy management commands may also be transmitted along with entitlement control messages (ECM), which are generally used by the conditional access unit to regulate access to a particular channel or service. Entitlement management messages (EMM) may be used to deliver privileges such as rights and de-scrambling keys. As known, a decryption or de-scrambling key is generally a code that is required to restore the scrambled data, and may be a function of the rights granted. Finally, content in the program data may include audio and video data, which may be in s scrambled or encrypted or clear format. In one embodiment, the program data receiver 110 is a television set where the digital receiver 112 is a set-top box integrated therein, and the decoder 114 is a Motion Picture Experts Group (MPEG) decoder.

The transmission medium 120 operates to transmit control information and data including program data between the program data receiver 110 and other components in the system 100. The transmission medium 120 may include air, fiber optics, electronic and magnetic media, computer network connection, telephone connection, and any other communication media.

The audio system 130 is coupled to the transmission medium 130 to provide audio services. The audio system 130 may include speakers, an audio player/recorder such as a compact disk player, or other magneto-optical disc that may be used to play and/or record audio data. The digital video recorder/player 140 is coupled to the transmission medium 120 to provide video services. The digital video recorder/player 140 may be used to record analog or digital video, audio, and other data transmissions. In one embodiment, the digital video recorder/player 140 may be used to replay or record the program data received by the program data receiver 110 and transmitted over the transmission medium 120.

The disk recording unit 150 may also be coupled to the program data receiver 110 and other components via the transmission medium 120. The disk recording unit 150 may be a personal computer system, a stand-alone hard disk recording unit, or other disk recording device capable of recording analog or digital audio, video and data transmissions, including the program data received and transmitted by the program data receiver 110.

The display 160 may include a television display, a monitor display or other devices capable of processing and displaying video signals. In one embodiment, the display 160 is a digital television set. The control unit 170 may also be coupled to the transmission medium 120 to coordinate and control the operation of some or each of the components on the system 100, as well as other devices remotely coupled thereto.

The network conditional access (CA) unit 180 may also be coupled to the transmission medium 120. The network CA unit 180 operates to re-scramble program data with content in clear format such that the system 100 supports the simultaneous transmission of program data in clear and scrambled format. The network CA unit 180 may be a CA device that operates as a second CA device in a system embodiment where the program data receiver 110 operates as a master CA device.

Figure 2:
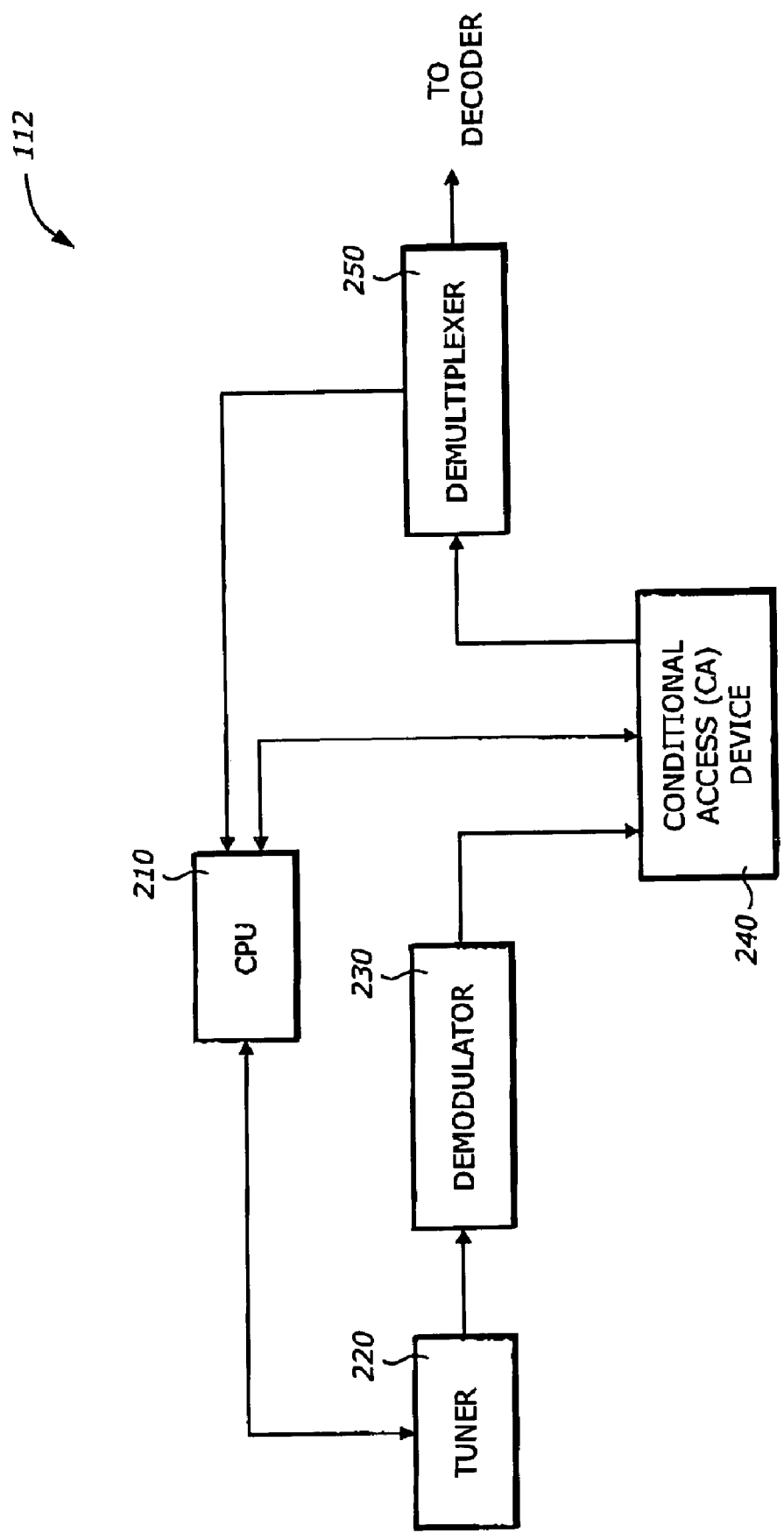
FIG. 2 is a diagram illustrating a digital receiver and a decoder according to one embodiment of the invention.

FIG. 2 is a diagram illustrating a digital receiver 112 according to one embodiment of the invention. The digital receiver 112 includes a central processing unit (CPU) 210, a tuner 220, a demodulator 230, a conditional access (CA) unit 240, and a demultiplexer 250.

The control processing unit 210 performs control functions for the tuner 220, the CA unit 240 and the demultiplexer 250. The CPU 210 may determine the frequency in which a channel is broadcast or otherwise transmitted. The CPU 210 may support a graphical user interface (GUI), such as electronic programming guide (EPG) to allow a user to navigate through various channels and program options to select a desired channel or program for viewing, listening, recording and the like.

The tuner 220 selects a frequency of the signal received by the program data receiver 110 (in FIG. 1) under the control of the CPU 210. The tuner 220 processes, amplifies, digitizes, and generates a bitstream to the demodulator 230.

The demodulator 230 demodulates the bitstream received from the tuner 220 to provide the program data as originally transmitted. The type of demodulation performed by the demodulator 230 depends on the type of transmission as well as the modulation process used in the transmission process. Examples of the demodulation includes quadrature amplitude modulation (QAM) demodulation, quadrature phase shift key (QPSK) demodulation, and vestigial side band (VSB) demodulation. In addition, the demodulator 230 may perform error correction on the received bitstream.

The conditional access unit 240 may be integral or external to the digital receiver 112. The CA unit 240 provides conditional access to the program data as provided by the demodulator 230. The program data is typically scrambled using an access key. The CA unit 240 may be used in an external or split mode. In the external mode, the CA unit 240 de-scrambles the program data content and decrypts the keys externally; e.g., as is the case with the National Renewable Security System (NRSS) conditional access modules. In a split conditional access unit, the program data content is de-scrambled within the digital receiver 112, while the key decryption is done externally, e.g., via a smart card.

The demultiplexer 250 receives the de-scrambled or unscrambled content from the CA unit 240. The demultiplexer 250 separates the system information from the content in the program data, and according to one embodiment, parses the program data for packet identifiers that are associated with the system information, audio information, and video information, and then transmits the system information to the control processing unit 210 and the audio and video information to the decoder 114 (in FIG. 1).

When the CA device 240 is used externally to the digital receiver 112, the digital receiver 112 is typically referred to as a host. In the following, a host is used to describe a digital receiver or any device or system that can provide a transport stream to the CA device. A digital device is any one of the audio system 130, the digital video recorder or player 140, the disk recording unit 150, the display 160 and the control unit 170 (shown in FIG. 1), or any combination thereof.

Figure 3:
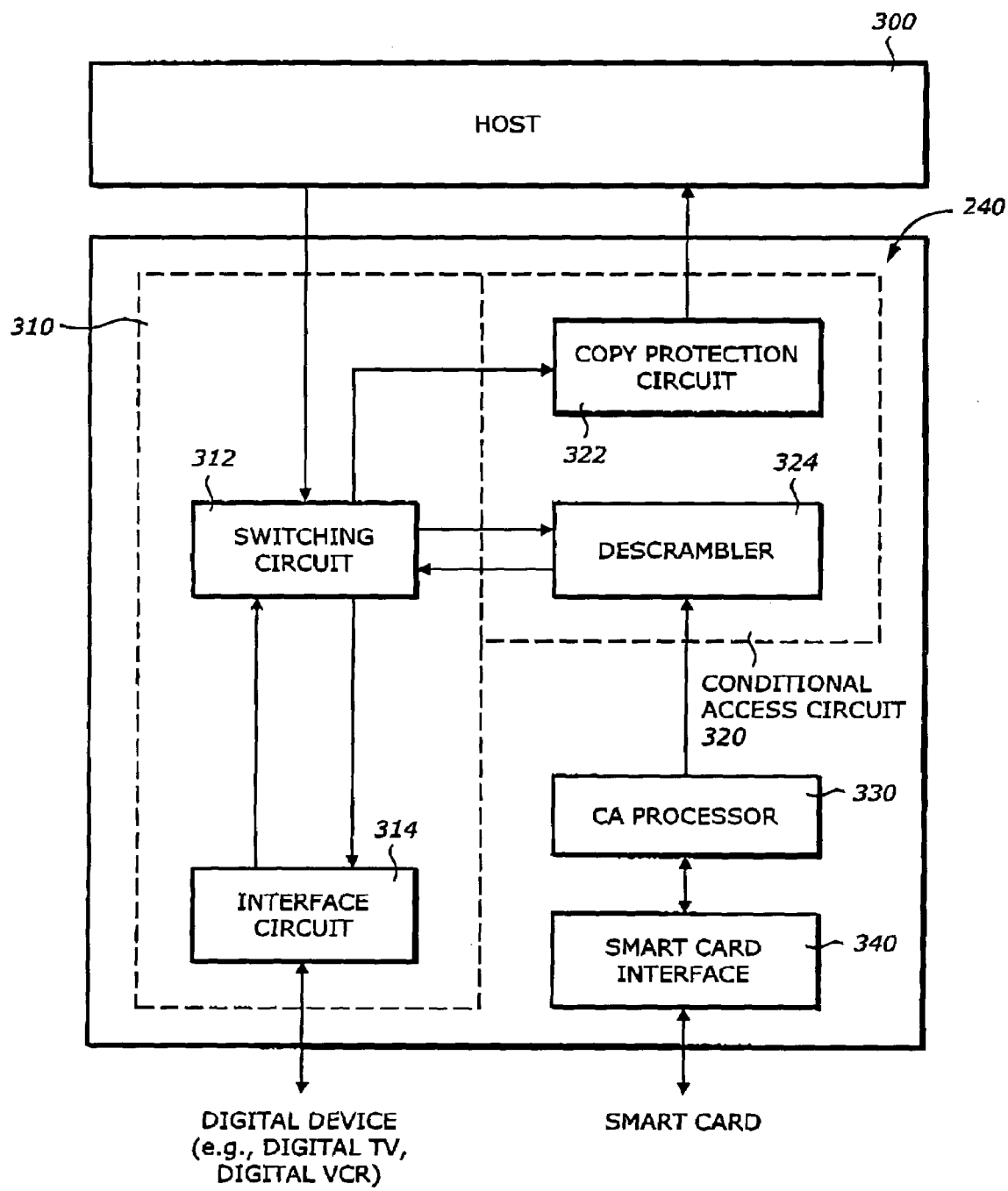
FIG. 3 is a diagram illustrating a conditional access system according to one embodiment of the invention.

FIG. 3 is a diagram illustrating a conditional access (CA) device 240 according to one embodiment of the invention. The CA device 240 includes a switching and interface circuit 310, a CA circuit 320, a CA processor 330, and a smart card interface 340.

The switching and interface circuit 310 is coupled to the host, the CA circuit 320 and the digital device to provide interface between the CA device 240 and the digital device. The switching and interface circuit 310 includes a switching circuit 312 and an interface circuit 314. The CA circuit 320 de-scrambles a stream and generates a copy-protected stream to the host. The CA circuit 320 includes a copy protection circuit 322 and a de-scrambler 324.

The switching circuit 312 is coupled to the host and the CA circuit 320 to switch input streams into output streams. The input streams include a host stream from the host, a de-scrambled stream from the de-scrambler 324, and an interface input stream from the interface circuit 314. The output streams include an interface output stream to the interface circuit 314, a de-scrambler input stream to the de-scrambler 324, and a copy stream to the copy-protection circuit 322.

The interface circuit 314 is coupled to the switching circuit 310 and a digital device to transfer the interface output stream from the switching circuit 310 to the digital device and the interface input stream from the digital device to the switching circuit 310. The interface circuit 314 convert the interface output stream into the corresponding interface protocol, and the stream from the digital device into the proper stream to the switching circuit 310. In one embodiment, the interface protocol is the 1394 serial interface protocol. The digital device may be any one of the audio system 130, the digital video recorder or player 140, the disk recording unit 150, the display 160 and the control unit 170 (shown in FIG. 1), or any combination thereof. It is contemplated that the digital device has a corresponding interface compatible with the interface circuit 314, e.g., supporting the same interface protocol.

The de-scrambler 324 receives and de-scrambles the de-scrambler input stream from the switching circuit 310 to generate the de-scrambled stream. The de-scrambler 324 receives the control and a de-scrambling key from the CA processor 330.

The copy protection circuit 322 receives the copy stream from the switching circuit 312 and generates a copy protected stream to the host. In general, the host then receives a de-scrambled and copy-protected stream from the CA device 300.

The CA processor 330 provides control and coordination of conditional access operations. The CA processor 330 may also provides control to the switching circuit 312 to control the switching or data selection functions. The smart card interface 340 provides interface to the smart card. In one embodiment, the smart card interface 340 is the PCMCIA card interface.

The switching circuit 312 provides a number of switching methods to the input streams to the output streams. Alternative embodiments exist to provide several data paths for the streams to be routed or steered within the switching circuit 312.

Figure 4A:
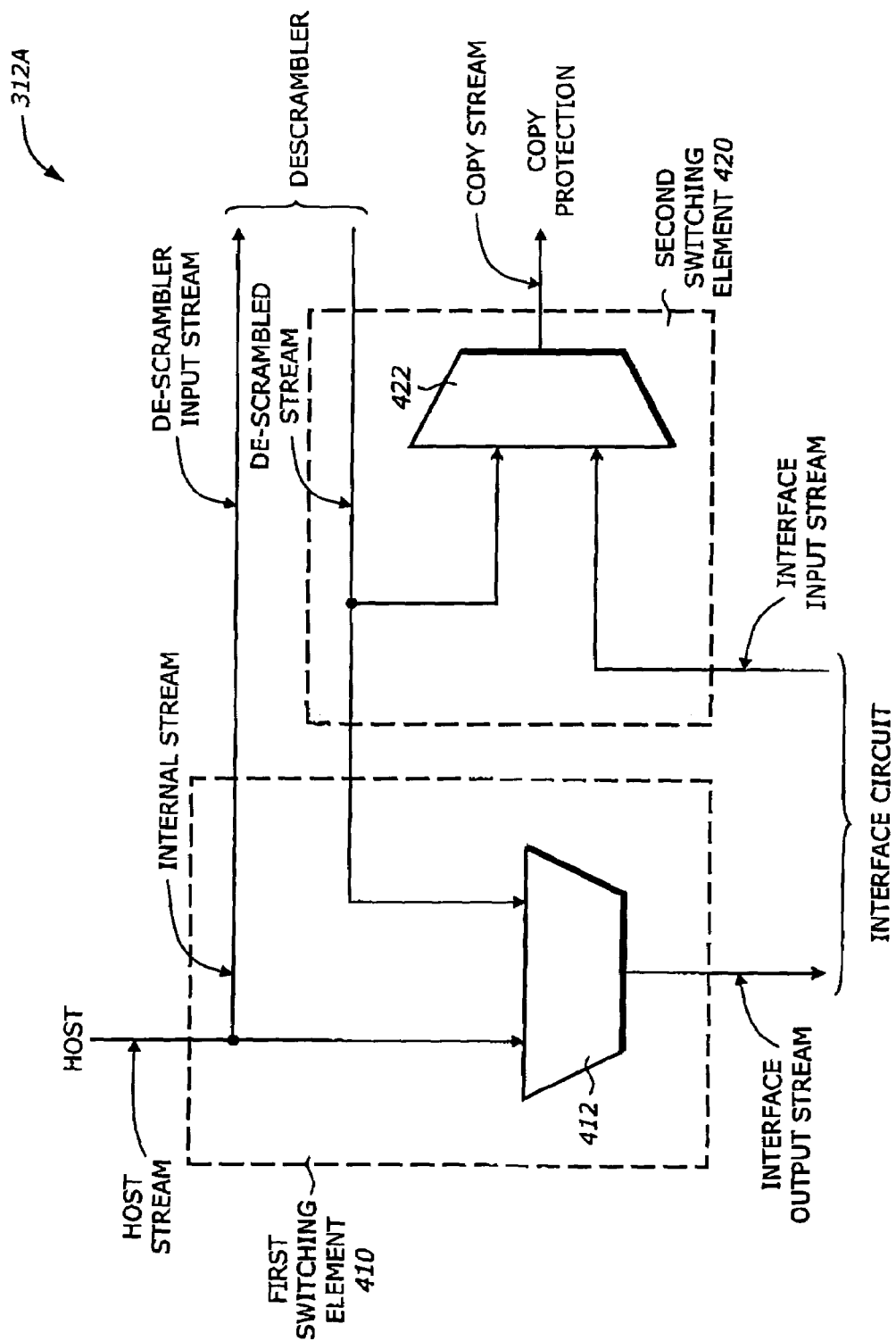
FIG. 4A is a diagram illustrating a switching circuit according to one embodiment of the invention.

FIG. 4A is a diagram illustrating a switching circuit 312A according to one embodiment of the invention. The switching circuit 312A includes a first switching element 410 and a second switching element 420.

The first switching element 410 receives the host stream from the host and the de-scrambled stream from the de-scrambler 324 (shown in FIG. 3). The host stream may be in a scrambled or clear format. The first switching element 410 generates an internal stream, and generates the de-scrambler input stream to the de-scrambler 324 and the interface output stream to the interface circuit 314.

The first switching element 410 includes a connection to connect the host stream to the internal stream and the de-scrambler input stream. In other words, the host stream is the internal stream and also the de-scrambler input stream. The first switching element 410 further includes a data selector, or multiplexer, 412. The data selector 412 receives at its inputs the host stream and the de-scrambled stream and provides the interface output stream. The data selector 412 may be controlled by the CA processor 330 (in FIG. 3).

The second switching element 420 includes a data selector 422. The data selector 422 receives at its inputs the interface input stream from the interface circuit 314 (in FIG. 3) and the de-scrambled stream from the de-scrambler 324 (in FIG. 3), and generates the copy stream to the copy protection circuit 322 (in FIG. 3). The data selector 422 may be controlled by the CA processor 330 (in FIG. 3).

The first and second switching elements 410 and 420 provide flexible data routing for the input and output streams. A number of scenarios exist. For example, the host stream may be in scrambled format and is routed to the de-scrambler 324. The de-scrambler 324 de-scrambles the scrambled host stream. The data selector 412 then selects the de-scrambled host stream to the interface output stream. The interface output stream is the host stream in the clear format. The interface circuit 314 then sends the clear host stream to the digital device such as a digital television for displaying the original content. In another scenario, the host stream may be in the clear format and can be delivered directly to the interface output stream via the data selector 412. The digital device may provide a return path of a clear stream to the switching element 420 to be sent to the copy protection circuit 322. The copy protection circuit 322 then provides a copy protected stream to the host.

Figure 4B:
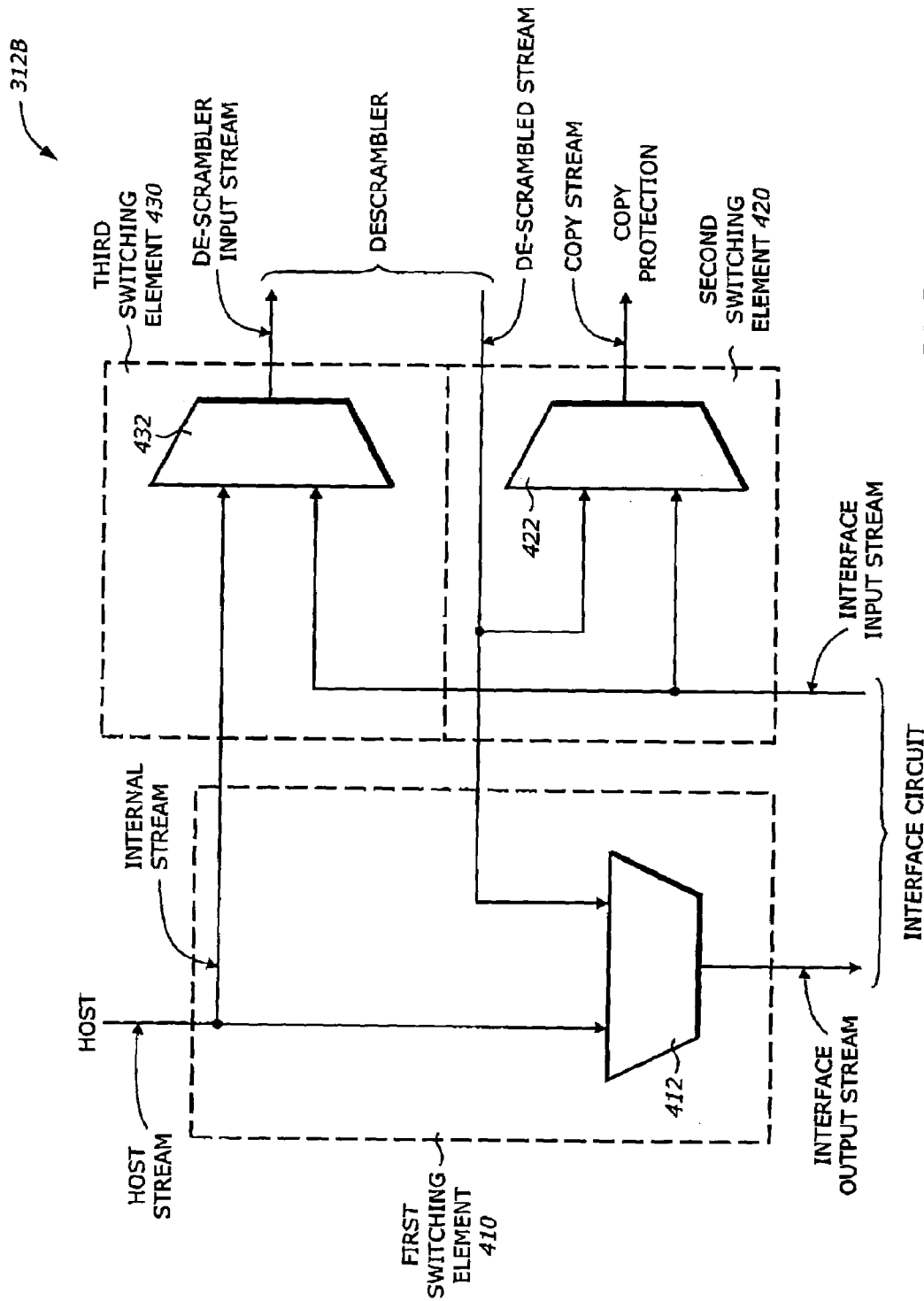
FIG. 4B is a diagram illustrating another switching circuit according to one embodiment of the invention.

FIG. 4B is a diagram illustrating a switching circuit 312B according to one embodiment of the invention. The switching circuit 312B includes the first and second switching elements 410 and 420 (in FIG. 4A) and a third switching element 430.

The third switching element 430 includes a data selector 432. The data selector 432 receives the internal stream from the first switching element 410 and the interface input stream from the interface circuit 314 (in FIG. 3), and provides the de-scrambler input stream to the de-scrambler 324 (in FIG. 3). The third switching element 430 may be controlled by the CA processor 330 (in FIG. 3).

The first, second, and third switching elements 410, 420, and 430, provide further flexible data routing for the input and output streams. With the addition of the third switching element 430, the de-scrambler input stream may be taken from the host stream or from the return stream provided by the digital device. The return stream from the digital device may be scrambled and is de-scrambled by the de-scrambler 324.

Figure 4C:
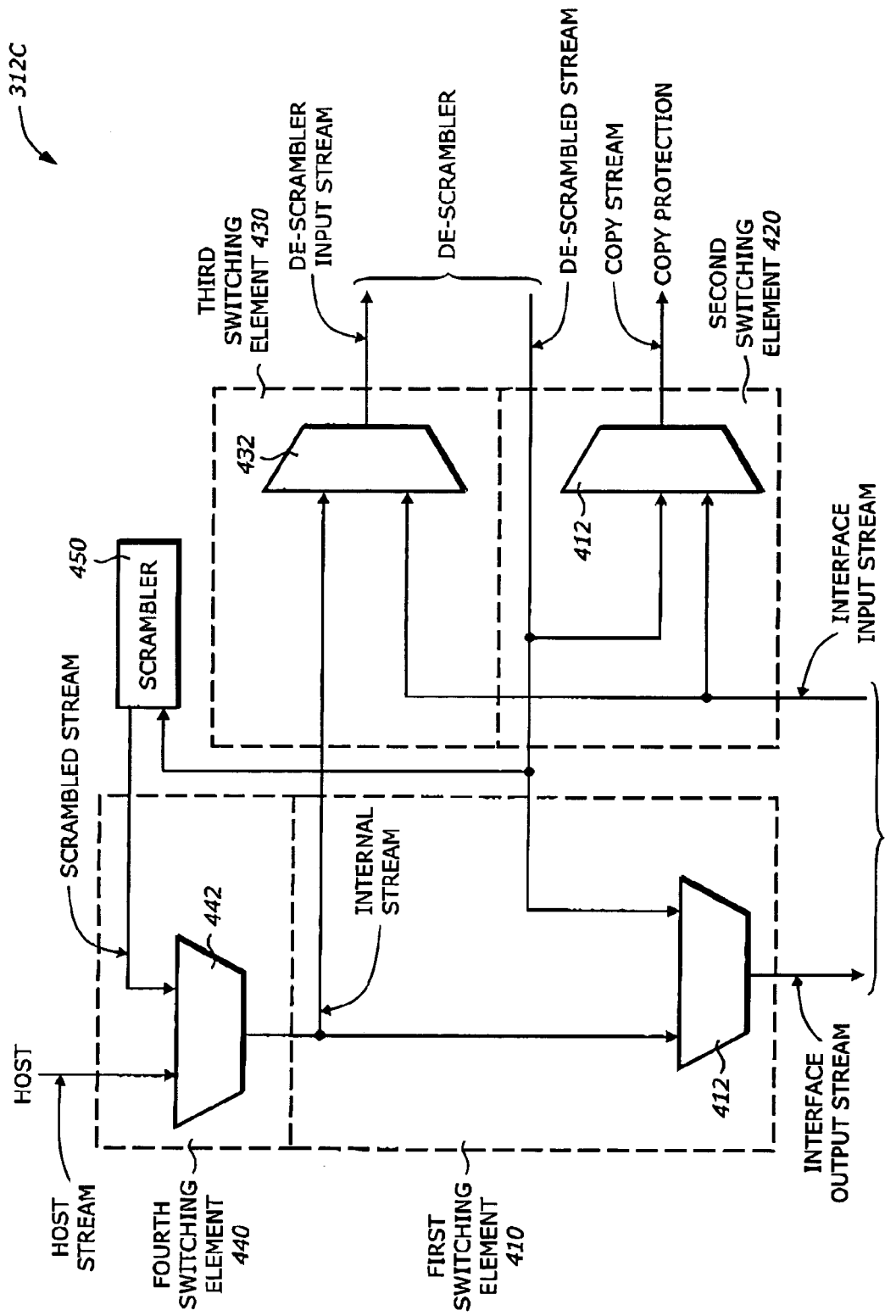
FIG. 4C is a diagram illustrating a switching circuit with a re-scrambler according to one embodiment of the invention.

FIG. 4C is a diagram illustrating a switching circuit 312C according to one embodiment of the invention. The switching circuit 312C includes the first, second, and third switching elements 410, 420, and 430 (in FIG. 4B), a fourth switching element 440, and a scrambler 450.

The fourth switching element 440 includes a data selector 442. The data selector receives the host stream and a scrambled stream from the scrambler, and generates the internal stream to the first switching element 410. The fourth switching element 440 may be controlled by the CA processor 330 (in FIG. 3).

The scrambler 450 receives the de-scrambled stream from the de-scrambler 324 and provides the scrambled stream to the fourth switching element 440. The scrambler 450 may act as a re-scrambler for the return stream from the digital device.

The first, second, third, and fourth switching elements 410, 420, 430, and 440, and the scrambler 450 provide further flexibility in data routing for the input and output streams. A number of scenarios exist. For example, a "store and playback" scheme can be supported which allows a scrambled content, either from the broadcast stream from the host or locally scrambled, to be recorded or played back through the switching and interface circuit. For example, a scrambled content may be provided by a digital device via the interface input stream. The scrambled content is then de-scrambled by the de-scrambler 324 via the switching element 430. This de-scrambled content is then re-scrambled by the scrambler 450 and goes through the switching elements 440 and 410 to the interface circuit 314. The re-scrambled content is then transferred to the same or different digital device via the interface circuit 314. At the same time, the de-scrambled content can be copy protected by the copy protection circuit via the switching element 420 and sent to the host.

While this invention has been described with reference to illustrative embodiments, this description is not intended to be construed in a limiting sense. Various modifications of the illustrative embodiments, as well as other embodiments of the invention, which are apparent to persons skilled in the art to which the invention pertains are deemed to lie within the spirit and scope of the invention.

What is claimed is:

1. An apparatus comprising:
   a switching circuit coupled to a host and a conditional access circuit to select at least an output stream from a plurality of input streams, the input streams including a host stream from the host, the at least output stream including an interface output stream; and
   an interface circuit coupled to the switching circuit and a digital device to transfer the interface output stream to the digital device.
2. The apparatus of claim 1 wherein the host stream is in one of scrambled and clear formats.
3. The apparatus of claim 2 wherein the conditional access circuit includes a de-scrambler and a copy protection circuit, the de-scrambler receiving a de-scamber input stream and generating a de-scrambled stream.
4. The apparatus of claim 3 wherein the at least output stream further includes one of a copy stream to the copy protection circuit and the de-scrambler input stream to the de-scrambler.
5. The apparatus of claim 4 wherein the input streams further include the de-scrambled stream from the de-scrambler and an interface input stream from the interface circuit.
6. The apparatus of claim 5 wherein the switching circuit comprises:
   a first switching element coupled to the host and the de-scrambler to provide the interface output stream from an internal stream and the de-scrambled stream; and
   a second switching element coupled to the digital device, the copy protection circuit and the de-scrambler to provide the copy stream from the de-scrambled stream and the interface input stream.
7. The apparatus of claim 6 wherein the internal stream provides the de-scrambler input stream and wherein the host stream provides the internal stream.
8. The apparatus of claim 6 further comprising:
   a third switching element coupled to the first switching element, the digital device and the de-scrambler to provide the de-scrambler input stream to the de-scrambler from the host stream and the interface input stream.
9. The apparatus of claim 8 further comprising:
   a fourth switching element coupled to the first and third switching elements to provide the internal stream from the host stream and a scrambled stream; and
   a scrambler coupled to the fourth switching element and the de-scrambler to provide the scrambled stream from the de-scrambled stream.
10. The apparatus of claim 1 wherein the interface circuit provides a 1394 serial interface.
11. A method comprising:
    selecting at least an output stream from a plurality of input streams by a switching circuit coupled to a host and a conditional access circuit, the input streams including a host stream from the host, the at least output stream including an interface output stream; and
    transferring the interface output stream to the digital device by an interface circuit.
12. The method of claim 11 wherein the host stream is in one of scrambled and clear formats.
13. The method of claim 12 wherein the conditional access circuit includes a de-scrambler and a copy protection circuit, the de-scrambler receiving a de-scrambler input stream and generating a de-scrambled stream.
14. The method of claim 13 wherein the at least output stream further include one of a copy stream to the copy protection circuit and the de-scrambler input stream to the de-scrambler.
15. The method of claim 14 wherein the input streams further include the de-scrambled stream from the de-scrambler and an interface input stream from the interface circuit.
16. The method of claim 15 wherein switching comprises:
    providing the interface output stream from an internal stream and the de-scrambled stream by a first switching element; and
    providing the copy stream from the de-scrambled stream and the interface input stream by a second switching element.
17. The method of claim 16 wherein the internal stream provides the de-scrambler input stream and wherein the host stream provides the internal stream.
18. The method of claim 16 further comprising:
    providing the de-scrambler input stream to the de-scrambler from the host stream and the interface input stream by a third switching element.
19. The method of claim 18 further comprising:
    providing the internal stream from the host stream and a scrambled stream by a fourth switching element; and
    providing the scrambled stream from the de-scrambled stream by a scrambler.
20. The method of claim 11 wherein the interface circuit provides a 1394 serial interface.
21. A system comprising:
    a host to provide a content;
    a conditional access device coupled to the host to provide conditional access to the content, the condition access device having a conditional access circuit;

a digital device coupled to the conditional access device to access the content; and a circuit coupled to the host and the digital device to provide interface between the conditional access device and the digital device, the comprising:

a switching circuit coupled to the host and the conditional access circuit to select at least an output stream from a plurality of input streams, the input streams including a host stream from the host, the at least output stream including an interface output stream, and an interface circuit coupled to the switching circuit and the digital device to transfer the interface output stream to the digital device.

22. The system of claim 21 wherein the host stream is in one of scrambled and clear formats.

23. The system of claim 22 wherein the conditional access circuit includes a de-scrambler and a copy protection circuit, the de-scrambler receiving a de-scrambler input stream and generating a de-scrambled stream.

24. The system of claim 23 wherein the at least output stream further includes one of a copy stream to the copy protection circuit and the de-scrambler input stream to the de-scrambler.

25. The system of claim 24 wherein the input streams further include the de-scrambled stream from the de-scrambler and an interface input stream from the interface circuit.

26. The system of claim 25 wherein the switching circuit comprises:

a first switching element coupled to the host and the de-scrambler to provide the interface output stream from an internal stream and the de-scrambled stream; and a second switching element coupled to the digital device, the copy protection circuit and the de-scrambler to provide the copy stream from the de-scrambled stream and the interface input stream.

27. The system of claim 26 wherein the internal stream provides the de-scrambler input stream and wherein the host stream provides the internal stream.

28. The system of claim 26 wherein the switching circuit further comprises:

a third switching element coupled to the first switching element, the digital device and the de-scrambler to provide the de-scrambler input stream to the de-scrambler from the host stream and the interface input stream.

29. The system of claim 28 wherein the switching circuit further comprises:

a fourth switching element coupled to the first and third switching elements to provide the internal stream from the host stream and a scrambled stream; and a scrambler coupled to the fourth switching element and the de-scrambler to provide the scrambled stream from the de-scrambled stream.

30. The system of claim 21 wherein the interface circuit provides a 1394 serial interface.

* * * * *